United States Patent [19]

Carroll et al.

[11] Patent Number: 4,714,761

[45] Date of Patent: Dec. 22, 1987

[54] 6,6-DIHALOPENICILLANIC ACID 1,1-DIOXIDES AND PROCESS

[75] Inventors: Ronnie D. Carroll, East Lyme; Robert A. Volkmann, Ledyard, both of Conn.

[73] Assignee: Pfizer Inc., New York, N.Y.

[21] Appl. No.: 890,708

[22] Filed: Jul. 25, 1986

Related U.S. Application Data

[63] Continuation of Ser. No. 226,076, Jan. 19, 1981, abandoned, which is a continuation of Ser. No. 17,808, Mar. 5, 1979, abandoned.

[51] Int. Cl.$^4$ .................. C07D 499/00; A61K 31/425
[52] U.S. Cl. ..................................... 540/310; 514/195
[58] Field of Search ................ 540/310, 350; 514/192, 514/195

[56] References Cited

U.S. PATENT DOCUMENTS

| | | | |
|---|---|---|---|
| 3,197,466 | 7/1965 | Chow et al. | 260/239.1 |
| 3,206,469 | 9/1965 | Pifferi | 260/307.7 |
| 3,741,959 | 6/1973 | Looker et al. | 260/239.1 |
| 4,203,992 | 5/1980 | Gordon et al. | 424/271 |
| 4,203,993 | 5/1980 | Gordon | 424/271 |
| 4,234,579 | 11/1980 | Barth | 260/246 |
| 4,420,426 | 12/1983 | Moore | 260/245.2 R |

FOREIGN PATENT DOCUMENTS

| | | |
|---|---|---|
| 866845 | 11/1978 | Belgium . |
| 881675 | 8/1980 | Belgium . |
| 13617 | 7/1980 | European Pat. Off. . |
| 2824535 | 12/1978 | Fed. Rep. of Germany . |
| 1072108 | 6/1967 | United Kingdom . |
| 2044255 | 10/1980 | United Kingdom . |

OTHER PUBLICATIONS

Cignarella et al., Journal of Organic Chemistry, 27, 2668 (1962).
Clayton, Journal of the Chemical Society (London), Part C, 2123 (1969).
Harrison et al., Journal of the Chemical Society (London), Perkin, I., 1772, (1976).
Busson et al., Recent Advances in the Chemistry of Beta-Lactam Antibiotics, Chapter 32, pp. 304–313 (1977).
Cartwright, et al., Nature, 278, 360 (1979).

Primary Examiner—Nicholas S. Rizzo
Attorney, Agent, or Firm—Connolly & Hutz

[57] ABSTRACT

A process for the preparation of penicillanic acid 1,1-dioxide and esters thereof readily hydrolyzable in vivo, which comprises oxidation of a 6,6-dihalopenicillanic acid, or an ester thereof readily hydrolyzable in vivo, to the corresponding 6,6-dihalopenicillanic acid 1,1-dioxide or ester thereof, followed by dehalogenation (e.g. by hydrogenolysis). The 6,6-dihalopenicillanic acid 1,1-dioxides and esters thereof readily hydrolyzable in vivo are novel intermediates. Penicillanic acid 1,1-dioxide, and esters thereof readily hydrolyzable in vivo, are known compounds which are useful as beta-lactamase inhibitors and for enhancing the effectiveness of certain beta-lactam antibiotics (e.g. the penicillins) in the treatment of bacterial infections in mammals, particularly humans.

7 Claims, No Drawings

6,6-DIHALOPENICILLANIC ACID 1,1-DIOXIDES AND PROCESS

CROSS REFERENCE TO RELATED APPLICATIONS

This is a continuation of application Ser. No. 226,076, filed Jan. 19, 1981, abandoned, which in turn is a continuation of application Ser. No. 17,808 filed Mar. 5, 1979, abandoned.

BACKGROUND OF THE INVENTION

This invention relates to a new chemical process, and to new chemical compounds useful as intermediates in said process. More particularly, it relates to a new chemical process for the preparation of penicillanic acid 1,1-dioxide and esters thereof readily hydrolyzable in vivo. Said new chemical process comprises oxidation of a 6,6-dihalopenicillanic acid or ester thereof readily hydrolyzable in vivo to the corresponding 1,1-dioxide, followed by dehalogenation. Said new chemical compounds useful as intermediates are 6,6-dihalopenicillanic acid 1,1-dioxides and esters thereof readily hydrolyzable in vivo.

Penicillanic acid 1,1-dioxide and esters thereof readily hydrolyzable in vivo are useful as beta-lactamase inhibitors and as agents which enhance the effectiveness of certain beta-lactam antibiotics when the latter are used to treat bacterial infections in mammals, particularly humans. Previously, penicillanic acid 1,1-dioxide and esters thereof readily hydrolyzable in vivo have been prepared from 6-bromopenicillanic acid, or ester thereof readily hydrolyzable in vivo, by debromination to give penicillanic acid, or ester thereof readily hydrolyzable in vivo, followed by oxidation to the 1,1-dioxide. See pending U.S. patent application Ser. No. 890,451, filed Mar. 29, 1978; Belgian Pat. No. 867,859, granted Dec. 6, 1978; and West German Offenlegungsschrift No. 2,824,535 for details of methods of preparing penicillanic acid 1,1-dioxide and esters thereof readily hydrolyzable in vivo.

6-Halopenicillanic acids have been disclosed by Cignarella et al., *Journal of Organic Chemistry*, 27, 2668 (1962) and in U.S. Pat. No. 3,206,469; hydrogenolysis of 6-halopenicillanic acids to penicillanic acid is disclosed in British Patent Specification No. 1,072,108.

Clayton, *Journal of the Chemical Society* (London), (C), 2123, (1969), discloses: (a) the preparation of 6,6-dibromo- and 6,6-diiodopenicillanic acid; (b) oxidation of 6,6-dibromopenicillanic acid with sodium periodate, to give a mixture of the corresponding sulfoxides; (c) hydrogenolysis of methyl 6,6-dibromopenicillanate to give methyl 6α-bromopenicillanate; (d) hydrogenolysis of 6,6-dibromopenicillanic acid, and its methyl ester, to give penicillanic acid and its methyl ester, respectively; and (e) hydrogenolysis of a mixture of methyl 6,6-diiodopenicillanate and methyl 6α-iodopenicillanate to give pure methyl 6α-iodopenicillanate.

Harrison et al., *Journal of the Chemical Society* (London), Perkin I, 1772 (1976), disclose oxidation of methyl 6,6-dibromopenicillanate with 3-chloroperbenzoic acid to give methyl 6,6-dibromopenicillanate 1,1-dioxide.

SUMMARY OF THE INVENTION

This invention relates to a process for the preparation of a compound of the formula

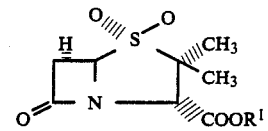

or a pharmaceutically-acceptable base salt thereof, wherein $R^1$ is selected from the group consisting of hydrogen and ester forming residues readily hydrolyzable in vivo, which comprises the steps of:

(a) contacting a compound of the formula

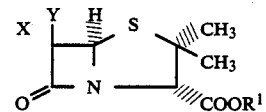

or a base salt thereof with a reagent selected from the group consisting of alkali metal permanganates, alkaline earth metal permanganates and organic peroxycarboylic acids, to give a compound of the formula

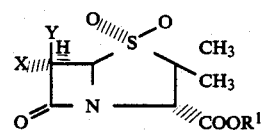

or a base salt thereof, wherein X and Y are each selected from the group consisting of chloro, bromo and iodo; provided that X and Y are not both chloro and X and Y are not both iodo; and (b) dehalogenating the compound of formula III.

A preferred way of carrying out step (b) comprises contacting the product of step (a) with hydrogen, in an inert solvent, at a pressure in the range from about 1 to about 100 kg/cm², at a temperature in the range from about 0° to about 60° C., and at a pH in the range from about 4 to about 9, and in the presence of a hydrogenolysis catalyst. The hydrogenolysis catalyst is usually present in an amount from about 0.01 to about 2.5 weight-percent, and preferably from about 0.1 to about 1.0 weight-percent, based on the dihalo-sulfone.

The preferred value for X and Y is bromo, and the preferred reagents for carrying out step (a) are potassium permanganate and 3-chloroperbenzoic acid.

In the case wherein X and Y are both chloro, the compound of formula II is difficult to obtain. In the case wherein X and Y are both iodo, step (a) of the process of this invention proceeds inconveniently slowly.

Also embraced within the ambit of this invention are the intermediates of formula III, wherein X, Y and $R^1$ are as defined above. A preferred intermediate is 6,6-dibromopenicillanic acid 1,1-dioxide, the compound of the formula III, wherein X and Y are bromo and $R^1$ is hydrogen.

DETAILED DESCRIPTION OF THE INVENTION

This invention relates to the preparation of compounds of the formula I, and to several intermediates therefor. Throughout this specification, these compounds are named as derivatives of penicillanic acid, which is represented by the following structural formula:

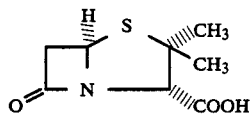
(IV)

In derivatives of penicillanic acid, broken line attachment of a substituent to the bicyclic nucleus indicates that the substituent is below the plane of the nucleus. Such a substituents is said to be in the alpha-configuration. Conversely, solid line attachment of a substituent to the bicyclic nucleus indicates that the substituent is above the plane of the nucleus. This latter configuration is referred to as the beta-configuration. Thus, the group X has the alpha-configuration and the group Y has the beta-configuration in formula II.

In this specification, when $R^1$ is an ester-forming residue readily hydrolyzable in vivo, it is a grouping which is notionally derived from an alcohol of the formula $R^1$—OH, such that the moiety $COOR^1$ in such a compound of formula I represents an ester grouping. Moreover, $R^1$ is of such a nature that the grouping $COOR^1$ is readily cleaved in vivo to liberate a free carboxy group (COOH). That is to say, $R^1$ is a group of the type when a compound of formula I, wherein $R^1$ is an ester-forming residue readily hydrolyzed in vivo, is exposed to mammalian blood or tissue, the compound of formula I, wherein $R^1$ is hydrogen, is readily produced. The groups $R^1$ are well known in the penicillin art. In most instances, they improve the absorption characteristics of the penicillin compound. Additionally, $R^1$ should be of such a nature that it imparts pharmaceutically-acceptable properties to a compound of formula II, and it liberates pharmaceutically-acceptable fragments when cleaved in vivo. The groups $R^1$ are well known and are readily identified by those skilled in the penicillin art, See, for example, West German Offenlegungsschrift No. 2,517,316. Specific examples of groups for $R^1$ are 3-phthalidyl, 4-crotonolactonyl, gamma-butyrolacton-4-yl and groups of the formula

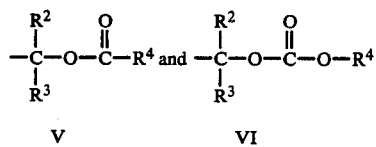

wherein $R^2$ and $R^3$ are each selected from the group consisting of hydrogen and alkyl having from 1 to 2 carbon atoms, and $R^4$ is alkyl having from 1 to 5 carbon atoms. However, preferred groups for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-alkoxycarbonyloxy)ethyl having from 5 to 8 carbon atoms, 3-phthalidyl, 4-crotonolactonyl and gamma-butyrolacton-4-yl.

3-Phthalidyl, 4-crotonolactonyl and gammabutyrolacton-4-yl refer to structures VII, VIII and IX. The wavy lines are intended to denote either of the two apimers or a mixture thereof.

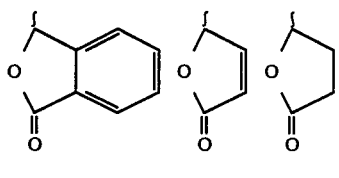

Step (a) of the process of this invention involves oxidation of the sulfide grouping in a compound of the formula II to a sulfone grouping, thereby producing a compound of the formula III. A wide variety of oxidants known in the art for the oxidation of sulfides to sulfones can be used for this process. However, particularly convenient reagents are alkali metal permanganates such as sodium and potassium permaganate; alkaline earth metal permanganates, such as calcium and barium permanganates; and organic peroxycarboxylic acids, such as peracetic acid and 3-chloroperbenzoic acid.

When a compound of the formula II, wherein X, Y and $R^1$ are as defined previously, is oxidized to the corresponding compound of the formula III, using a metal permanganate, the reaction is usually carried out by treating the compound of the formula II with from about 0.5 to about ten molar equivalents, and preferably from about one to about four molar equivalents, of the permangnate in an appropriate, reaction-inert solvent system. An appropriate, reaction-inert solvent system is one that does not adversely interact with either the starting materials or the product, and water is commonly used. If desired, a cosolvent which is miscible with water but will not interact with the permaganate, such as tetrahydrofuran, can be added. The reaction can be carried out at a temperature in the range from about $-30°$ to about $50°$ C., and it is preferably carried out from about $-10°$ to about $10°$ C. At about $0°$ C. the reaction is normally substantially complete within a short period, e.g. within one hour. Although the reaction can be carried out under neutral, basic or acid conditions, it is preferable to operate at a pH in the range from about 4 to about 9, preferably 6–8. However, it is essential to choose conditions which avoid decomposition of the beta-lactan ring system of the compound of the formulae II or III. Indeed, it is often advantageous to buffer the pH of the reaction medium in the vicinity of neutrality. The product is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula II wherein X, Y and $R^1$ are as previously defined, is oxidized to the corresponding compound of the formula III using a peroxycarboxylic acid, the reaction is usually carried out by treating the compound of the formula II with from about 1 to about 6 molar equivalents, and preferably about 2.2 molar equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about −30° to about 50° C., and preferably from about 15° to about 30° C. At about 25° C., reaction times of about 2 to about 16 hours are commonly used. The product is normally isolated by removal of the solvent by evaporation in vacuo. The reaction product can be purified by conventional methods, well known in the art. Alternatively, it can be used directly in step (b) without further purification.

Step (b) of the present process is a dehalogenation reaction. One convenient method of carrying out this transformation is to stir or shake a solution of a compound of the formula III under an atmosphere of hydrogen, or hydrogen mixed with an inert diluent such as nitrogen or argon, in the presence of a hydrogenolysis catalyst. Suitable solvents for this hydrogenolysis reaction are those which substantially dissolve the starting compound of the formula III but which do not themselves suffer hydrogenation or hydrogenolysis. Examples of such solvents include ethers such as diethyl ether, tetrahydrofuran, dioxan and 1,2-dimethoxyethane; low molecular weight esters such as ethyl acetate and butyl acetate; tertiary amides such as N,N-dimethylformamide, N,N-dimethylacetamide and N-methylpyrrolidone; water; and mixtures thereof. Additionally, it is usual to buffer the reaction mixture so as to operate at a pH in the range from about 4 to 9, and preferably from about 6 to 8. Borate and phosphate buffers are commonly used. Introduction of the hydrogen gas into the reaction medium is usually accomplished by carrying out the reaction in a sealed vessel, containing the compound of formula III, the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 20 hours. The catalysts used in this hydrogenolysis reaction are the type of agents known in the art for this kind of transformation, and typical examples are the noble metals, such as nickel, palladium, platinum and rhodium. The catalyst is usually present in an amount from about 0.01 to about 2.5 weight-percent, and preferably from about 0.1 to about 1.0 weight-percent, based on the compound of formula III. It is often convenient to suspend the catalyst on an inert support; a particularly convenient catalyst is palladium suspended on an inert support such as carbon.

Other methods can be used for reductive removal of the halogen from a compound of formula III, i.e. step (b). For example, X and Y can be removed using a dissolving metal reducing system, such as zinc dust in acetic acid, formic acid or a phosphate buffer, according to well-known procedures. Alternatively, step (b) can be carried out using a tin hydride, for example a trialkyltin hydride such as tri-n-butyltin hydride.

As will be appreciated by one skilled in the art, when it is desired to prepare a compound of the formula I, wherein $R^1$ is hydrogen, a compound of the formula II, wherein $R^1$ is hydrogen, can be subjected to steps (a) and (b) of the process disclosed and claimed herein. In other words, the process comprises oxidation, followed by dehalogenation, of a 6,6-dihalopenicillanic acid with a free carboxy group at the 3-position. However, in a further aspect of this invention, it is possible to operate either of steps (a) and (b) with the carboxy group at the 3-position blocked by a conventional penicillin carboxy protecting group. The protecting group can be removed after step (a) or step (b), with regeneration of the free carboxy group. In this regard, a variety of protecting group conventionally used in the penicillin art to protect the 3-carboxy group can be employed. The identity of the protecting group is not critical. The only requirements for the protecting group are that: (i) it must be stable during the individual step (a) or step (b); and (ii) it must be removable from the particular compound of formula I or III, using conditions under which the beta-lactam ring system remains substantially intact. For each of steps (a) and (b), typical examples are the tetrahydropyranyl group, trialkylsilyl groups, the benzyl group, substituted benzyl groups (e.g. 4-nitrobenzyl), the benzhydryl group, the 2,2,2-trichloroethyl group, the t-butyl group and the phenacyl group. Although all protecting groups are not operable in all situations, a particular group which can be used in a particular situation will be readily selected by one skilled in the art. See further: U.S. Pat. Nos. 3,632,850 and 3,197,466; British Pat. No. 1,041,985, Woodward et al, *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporin and Penicillins, Chemistry and Biology", edited by H. E. Flynn, Academic Press, Inc., 1972. The penicillin carboxy protecting group is removed in conventional manner, having due regard for the lability of the beta-lactam ring system.

The compound of formula I, wherein $R^1$ is hydrogen, is acidic and will form salts with basic agents. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate. Preferred salts of the compound of the formula I are the sodium, potassium and triethylamine salts.

The compound of formula I, wherein $R^1$ is hydrogen, and the salts thereof are active as antibacterial agents of medium potency both in vitro and in vivo, and the compounds of formula I, wherein $R^1$ is an ester-forming residue readily hydrolyzable in vivo are active as antibacterial agents of medium potency in vivo. Minimum inhibitory concentrations (MIC'S) of penicillanic acid 1,1-dioxide against several microorganisms are shown in Table I.

TABLE I

In Vitro Antibacterial Activity of Penicillanic Acid 1,1-Dioxide

| Microorganism | MIC (mcg./ml.) |
| --- | --- |
| Staphylococcus aureus | 100 |
| Streptococcus faecalis | 200 |
| Streptococcus pyogenes | 100 |
| Escherichia coli | 50 |
| Pseudomonas aeruginosa | 200 |
| Klebsiella pneumoniae | 50 |
| Proteus mirabilis | 100 |
| Proteus morgani | 100 |
| Salmonella typhimurium | 50 |
| Pasteurella multocida | 50 |
| Serratia marcescens | 100 |
| Enterobacter aerogenes | 25 |
| Enterobacter clocae | 100 |
| Citrobacter freundii | 50 |
| Providencia | 100 |
| Staphylococcus epidermis | 200 |
| Pseudomonas putida | 200 |
| Hemophilus influenzae | 50 |
| Neisseria gonorrhoeae | 0.312 |

The in vitro antibacterial activity of the compound of the formula I, wherein $R^1$ is hydrogen, and its salts, makes them useful as industrial antimicrobials, for example in water treatment, slime control, paint preservation and wood preservation, as well as for topical application as disinfectants. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

The in vivo activity of the compounds of formula I wherein $R^1$ is hydrogen or an ester-forming residue readily hydrolyzable in vivo, and the salts thereof, makes them suitable for the control of bacterial infections in mammals, including man, by both the oral and parenteral modes of administration. The compounds will find use in the control of infections caused by susceptible bacteria in human subjects, e.g. infections caused by strains of *Neisseria gonorrhoeae*.

When considering therapeutic use of a compound of the formula I, or a salt thereof, in a mammal, particularly man, the compound can be administered alone, or it can be mixed with pharmaceutically acceptable carriers or diluents. It can be administered orally or paranterally, i.e. instramuscularly, subcutaneously or intraperitoneally. The carrier or diluent is chosen on the basis of the intended mode of administration. For example, when considering the oral mode of administration, the compound can be used in the form of tablets, capsules, lozenges, troches, powders, syrups, slixirs, aqueous solutions and suspensions, and the like, in accordance with standard pharmaceutical practice. The proportional ratio of active ingredient to carrier will depend on the chemical nature, solubility and stability of the active ingredient, as well as the dosage contemplated. However, pharmaceutical compositions containing an antibacterial agent of the formula I will likely contain from about 20% to about 95% of active ingredient. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient can be combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

The prescribing physician will ultimately determine the appropriate dose of a compound of formula I for a given human subject, and this can be expected to vary according to the age, weight, and response of the individual patient, as well as the nature and the severity of the patient's symptoms. The compound will normally be used orally at dosages in the range from about 10 to about 200 mg. par kilogram of body weight per day, and parenterally at dosages from about 10 to about 400 mg. per kilogram of body weight per day. These figures are illustrative only, however, and in some cases it may be necessary to use dosages outside these limits.

The compounds of the formula I, wherein $R^1$ is hydrogen or an ester-forming residue readily hydrolyzable in vivo, or a salt thereof, enhance the antibacterial effectiveness of beta-lactam antibiotics in vivo. They lower the amount of the antibiotic which is needed to protect mice against an otherwise lethal inoculum of certain beta-lactamase producing bacteria. This ability makes them valuable for co-administration with beta-lactam antibiotics in the treatment of bacterial infections in mammals, particularly man. In the treatment of a bacterial infection, said compound of the formula I can be comingled with the beta-lactam antibiotic, and the two agents thereby administered simultaneously. Alternatively, said compound of the formula I can be administered as a separate agent during a course of treatment with a beta-lactam antibiotic. In some instances it is advantageous to pre-dose the subject with the compound of the formula I before initiating treatment with a beta-lactam antibiotic.

When using penicillanic acid 1,1-dioxide, a salt or an ester thereof readily hydrolyzable in vivo to enhance the effectiveness of beta-lactam antibiotic, it is administered preferably in formulation with standard pharmaceutical carriers or diluents. The methods of formulation discussed earlier for use of penicillanic acid 1,1-dioxide or an ester thereof readily hydrolyzable in vivo as a single-entity antibacterial agent can be used when co-administration with another beta-lactam antibiotic is intended. A pharmaceutical composition comprising a pharmaceutically-acceptable carrier, a beta-lactam antibiotic and penicillanic acid 1,1-dioxide or a readily hydrolyzable ester thereof will normally contain from about 5 to about 80 percent of the pharmaceutically acceptable carrier by weight.

When using penicillanic acid 1,1-dioxide or an ester thereof readily hydrolyzable in vivo in combination with another beta-lactam antibiotic, the sulfone can be administered orally or parenterally, i.e. intramuscularly, subcutaneously or intraperitoneally. Although the prescribing physician will ultimately decide the dosage to be used in a human subject, the ratio of the daily dosages of the penicillanic acid 1,1-dioxide or salt or ester thereof and the beta-lactam antibiotic will normally be in the range from about 1:3 to 3:1. Additionally, when using penicillanic acid 1,1-dioxide or salt or ester thereof readily hydrolyzable in vivo in combination with another beta-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some cases it may be necessary to use dosages outside these limits.

Typical beta-lactam antibiotics with which penicillanic acid 1,1-dioxide and its esters readily hydrolyzable in vivo can be co-administered are:
6-(2-phenylacetamido)penicillanic acid,
6-(D-2-amino-2-phenylacetamido)penicillanic acid,
6-(2-carboxy-2-phenylacetamido)penicillanic acid, and
7-(2-(1-tetrazolyl)acetamido)-3-(2-[5-methyl-1,3,4-thiadiazolyl]thiomethyl)-3-desacetoxymethylcephalosporanic acid.

Typical microorganisms against which the antibacterial activity of the above beta-lactam antibiotics is enhanced are:
*Staphylococcus aureus,*
*Haemophilus influenzae,*
*Klebsiella pneumoniae,* and
*Bacteroides fragilis.*

As will be appreciated by one skilled in the art, some beta-lactam compounds are effective when administered orally or parenterally, while others are effective only when administered by the parenteral route. When penicillanic acid 1,1-dioxide, a salt or an ester thereof readily hydrolyzable in vivo, is to be used simultaneously (i.e. co-mingled) with a beta-lactam antibiotic which is effective only on parenteral administration, a combination formulation suitable for parenteral use will be required. When the penicillanic acid 1,1-dioxide or ester thereof is to be used simultaneously (co-mingled) with a beta-lactam antibiotic which is effective orally or parenterally, combinations suitable for either oral or parenteral administration can be prepared. Additionally, it is possible to administer preparations of the penicillanic acid 1,1-dioxide or salt or ester thereof orally, while at the same time administering a further beta-lactam antibiotic parenterally; and it is also possible to administer preparations of the penicillanic acid 1,1-dioxide or salt or ester thereof parenterally, while at the same time administering the further beta-lactam antibiotic orally.

Further details concerning the use and synthesis of compounds of the formula I are disclosed in West German Offenlegungsschrift No. 2,824,535.

The following examples and preparations are provided solely for the purpose of further illustration. Infrared (IR) spectra were measured as potassium bromide discs (KBr discs), and diagnostic absorption bands are reported in wave numbers ($cm^{-1}$). Nuclear magnetic resonance spectra (NMR) were measured at 60 MHz for solutions in deuterochloroform ($CDCl_3$), perdeutero dimethyl sulfoxide ($DMSO-d_6$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

6,6-Dibromopenicillanic Acid 1,1-Dioxide

To the dichloromethane solution of 6,6-dibromopenicillanic acid from Preparation A was added 300 ml of water, followed by the dropwise addition over a period of 30 minutes of 105 ml of 3N sodium hydroxide. The pH stabilized at 7.0. The aqueous layer was removed and the organic layer was extracted with water (2×100 ml). To the combined aqueous solutions was added, at −5° C., a premixed solution prepared from 59.25 g of potassium permanganate, 18 ml of concentrated phosphoric acid and 600 ml of water, until the pink color of the permanganate persisted. The addition took 50 minutes and 550 ml of oxidant were required. At this point 500 ml of ethyl acetate was added and then the pH was lowered to 1.23 by the addition of 105 ml of 6N hydrochloric acid. Then 250 ml of 1M sodium bisulfite was added during 10–15 minutes at ca. 10° C. During the addition of the sodium bisulfite solution the pH was maintained at 1.25–1.35 using 6N hydrochloric acid. The aqueous phase was saturated with sodium chloride and the two phases were separated. The aqueous solution was extracted with additional ethyl acetate (2×150 ml) and the combined ethyl acetate solutions were washed with brine and dried ($MgSO_4$). This afforded an ethyl acetate solution of 6,6-dibromopenicillanic acid 1,1-dioxide.

The 6,6-dibromopencillanic acid 1,1-dioxide can be isolated by removal of the solvent in vacuo. A sample so isolated from an analogous preparation had a melting point of 201° C. (dec.). The NMR spectrum ($CDCl_3/DMSO-d_6$) showed absorption at 9.35 (s,1H), 5.30 (s, 1H), 4.42 (s, 1H), 1.63 (s, 3H) and 1.50 (s, 3H)ppm. The IR spectrum (KBr disc) showed absorptions at 3846–2500, 1818, 1754, 1342 and 1250–1110 $cm^{-1}$.

EXAMPLE 2

6-Chloro-6-iodopenicillanic Acid 1,1-Dioxide

To a solution of 4.9 g of 6-chloro-6-iodopencillanic acid in 50 ml of dichloromethane was added 50 ml of water and then the pH was raised to 7.2 using 3N sodium hydroxide. The layers were separated and the aqueous layer was cooled to 5° C. To this solution was then added, dropwise, over a 20 minute period, a premixed solution prepared from 2.61 g of potassium permanganate, 1.75 ml of concentrated phosphoric acid and 50 ml of water. The pH was maintained at 6, and the temperature was maintained below 10° C., during the addition. At this point, 100 ml of ethyl acetate was added and the pH was adjusted to 1.5. To the mixture was then added 50 ml of 10% sodium bisulfite, keeping the temperature below 10° C. and the pH at ca 1.5 by the addition of 6N hydrochloric acid. The pH was lowered to 1.25 and the layers were separated. The aqueous layer was saturated with sodium chloride and extracted with ethyl acetate. The combined organic solutions were washed with brine, dried ($MgSO_4$) and evaporated in vacuo to give 4.2 g of the title compound, mp 143°–145° C. The NMR spectrum (CDCl$_3$) showed absorptions at 4.86 (s, 1H), 4.38 (S, 1H), 1.60 (s, 3H) and 1.43 (s, 3H)ppm. The IR spectrum (KBr disc) showed absorptions at 1800, 1740 and 1250–1110 cm$^1$.

EXAMPLE 3

6-Bromo-6-iodopenicillanic Acid 1,1-Dioxide

To a solution of 6.0 g of 6-bromo-6-iodopenicillanic acid in 50 ml of dichloromethane was added 50 ml of water. The pH was raised to 7.3 using 3N sodium hydroxide and the aqueous layer was removed. The organic layer was extracted with 10 ml of water. The combined aqueous phases were cooled to 5° C., and a premixed solution of 284 g of potassium permanganate in 2 ml of concentrated phosphoric acid and 50 ml of water was added dropwise, between 5° and 10° C. The addition took 20 minutes. At this point, 50 ml of ethyl acetate was added and the pH of the mixture was lowered to 1.5 using 6N hydrochloric acid. To this two-phase system was added, dropwise, 50 ml of 10% sodium bisulfite, maintaining the pH at about 1.5 by the addition of 6N hydrochloric acid. An additional 50 ml of ethyl acetate was added, and then the pH was lowered to 1.23. The layers were separated and the aqueous layer was saturated with sodium chloride. The saturated solution was extracted with ethyl acetate (3×50 ml) and the combined ethyl acetate layers were washed with brine, dried (MgSO$_4$) and evaporated in vacuo. The residue was dried under high vacuum, leaving 4.2 g of the title compound, mp 145–147. The NMR spectrum (CDCl$_3$) showed absorptions at 4.90 (s, 1H), 4.30 (s, 1H), 1.60 (s, 3H) and 1.42 (s, 3H)ppm. The IR spectrum (KBr disc) showed absorptions at 1800, 1740, 1330 and 1250–1110 cm$^1$.

EXAMPLE 4

6-Chloro-6-bromopenicillanic Acid 1,1-Dioxide

Oxidation of 6-chloro-6-bromopenicillanic acid with potassium permangenate, according to the procedure of Example 3, affords 6-chloro-6-bromopenicillanic acid 1,1-dioxide.

EXAMPLE 5

Penicillanic Acid 1,1-Dioxide

The ethyl acetate solution of 6,6-dibromopenicillanic acid 1,1-dioxide from Example 1 was combined with 705 ml of saturated sodium bicarbonate solution and 8.88 g of 5% palladium-on-carbon catalyst. The mixture was shaken under an atmosphere of hydrogen, at a pressure of about 5 kg/cm$^2$ for about 1 hour. The catalyst was removed by filtration, and the pH of the aqueous phase of the filtrate was adjusted to 1.2 with 6N hydrochloric acid. The aqueous phase was saturated with sodium chloride. The layers were separated and the aqueous phase was extracted with further ethyl acetate (3×200 ml). The combined ethyl acetate solutions were dried (MgSO$_4$) and evaporated in vacuo to afford 33.5 g (58% yield from 6-aminopenicillanic acid) of penicillanic acid 1,1-dioxide. This product was dissolved in 600 ml of ethyl acetate, the solution was decolorized using activated carbon and the solvent was removed by evaporation in vacuo. The product was washed with hexane. This afforded 31.0 g of pure product.

EXAMPLE 6

Hydrogenolysis of each of 6-chloro-6-iodopenicillanic acid 1,1-dioxide, 6-bromo-6-iodopenicillanic acid and 6-chloro-6-bromopenicillanic acid, respectively, according to the procedure of Example 5, affords, in each case, penicillanic acid 1,1-dioxide.

EXAMPLE 7

Penicillanic Acid 1,1-Dioxide

To a stirred suspension of 786 mg of 6-chloro-6-iodopenicillanic acid 1,1-dioxide in 10 ml of benzene was added 0.3 ml of triethylamine followed by 0.25 ml of trimethylsilyl chloride, at ca 0° C. Stirring was continued for 5 minutes at ca 0° C. and then at the reflux temperature of the solvent for 30 minutes. The reaction mixture was cooled to 25° C. and the precipitated material was removed by filtration. The filtrate was cooled to ca 0° C. and 1.16 g of tri-n-butyltin hydride and a few milligrams of azobisiscbutyronitrile were added. The reaction mixture was stirred and irradiated with ultraviolet light for 1 hour at ca 0° C. and then for 3.5 hours at the reflux temperature of the solvent. A further quantity of tri-n-butyltin hydride (1.1 ml) and a catalytic amount of azobisisobutyronitrile were added and stirring and irradiation at the reflux temperature were continued for an additional 1 hour. The reaction mixture was then poured into 50 ml of cold 5% sodium bicarbonate and the two-phase system was stirred for 30 minutes. Ethyl acetate (50 ml) was added and the pH was adjusted to 1.5 with 6N hydrochloric acid. The layers were separated and the aqueous layer was extracted with ethyl acetate. The combined ethyl acetate solutions were washed with brine, dried (MgSO$_4$) and evaporated in vacuo. The residue was triturated under hexane and then recovered by filtration. This afforded 0.075 mg of the title compound.

EXAMPLE 8

Penicillanic Acid 1,1-Dioxide

To a stirred suspension of 0.874 g of 6-bromo-6-iodopenicillanic acid 1,1-dioxide in 10 ml of benzene at ca 5° C., was added 0.3 ml of triethylamine followed by 0.25 ml of trimethylsilyl chloride. Stirring was continued at ca 5° C. for 5 minutes and then for 30 minutes at the reflux temperature of the solvent. The reaction mixture was cooled to room temperature and the solids were removed by filtration. The filtrate was cooled to ca 5° C., and 1.05 ml of tri-n-butyltin hydride and a catalytic amount of azobisisobutyronitrile were added. The mixture was irradiated with ultraviolet light for 1 hour at ca 5° C., and then it was poured into 30 ml of cold 5% sodium bicarbonate. The mixture was stirred for 30 minutes and then 50 ml of ethyl acetate were added. The mixture was acidified to pH 1.5 and the layers were separated. The aqueous layer was extracted with ethyl acetate (2×25 ml) and the combined ethyl acetate layers were washed with brine, dried (MgSO$_4$) and evaporated in vacuo. The residue was dried under high vacuum and the 30 ml of hexane was added. The insoluble material was recovered by filtration, affording 0.035 g of the title compound.

EXAMPLE 9

Pivaloyloxymethyl 6,6-Dibromopenicillanate 1,1-Dioxide

To a solution of 4.73 g of pivaloyoxymethyl 6,6-dibromopenicillanate in 15 ml of dichloromethane is added 3.80 g of 3-chloroperbenzoic acid at 0° to 5° C. The reaction mixture is stirred at 0° to 5° C. for 1 hour and then at 25° C. for 24 hours. The filtered reaction mixture is evaporated to dryness in vacuo and the residue is partitioned between ethyl acetate and water. The pH of the aqueous phase is adjusted to 7.5, and the layers are separated. The ethyl acetate phase is dried ($Na_2SO_4$) and evaporated in vacuo to give the title compound.

EXAMPLE 10

Oxidation of each of the 6,6-dihalopenicillanic acid esters of Preparation F using 3-chloroperbenzoic acid, according to the procedure of Example 9, affords the following compounds:
3-phthalidyl 6,6-dibromopenicillanate 1,1-dioxide,
4-crotonolactonyl 6-chloro-6-iodopenicillanate, 1,1-dioxide,
γ-butyrolactonyl 6-bromo-6-iodopencillanate 1,1-dioxide,
acetoxymethyl 6-chloro-6-bromopenicillanate 1,1-dioxide,
pivaloyloxymethyl 6-chloro-6-iodopenicillanate 1,1-dioxide,
hexanoyloxymethyl 6,6-dibromopenicillanate 1,1-dioxide,
1-(acetoxy)ethyl 6,6-dibromopenicillanate 1,1-dioxide,
1-(isobutyryloxy)ethyl 6-bromo-6-iodopenicillanate 1,1-dioxide,
1-methyl-1-(acetoxy)ethyl 6,6-dibromopenicillanate 1,1-dioxide,
1-methyl-1-(hexanoyloxy)ethyl 6-chloro-6-bromopenicillanate,
methoxycarbonyloxymethyl 6,6-dibromopenicillanate 1,1-dioxide,
propoxycarbonyloxymethyl 6-chloro-6-iodopenicillanate 1,1-dioxide,
1-(ethoxycarbonyloxy)ethyl 6,6-dibromopenicillanate 1,1-dioxide,
1-(butoxycarbonyloxy)ethyl 6-bromo-6-iodopenicillanate 1,1-dioxide,
1-methyl-1-(methoxycarbonyloxy)ethyl 6,6-dibromopenicillanate 1,1-dioxide and
1-methyl-1-(isopropoxycarbonyloxy)ethyl 6,6-dibromopenicillanate 1,1-dioxide, respectively.

EXAMPLE 11

Pivaloyloxymethyl Penicillanate 1,1-Dioxide

To a solution of 1.0 g of pivaloyloxymethyl 6,6-dibromopenicillanate 1,1-dioxide in 10 ml of methanol is added 3 ml of 1M sodium bicarbonate and 200 mg of 10% palladium on carbon. The reaction mixture is shaken vigorously under an atmosphere of hydrogen, at a pressure of about 5 kg/cm², until hydrogen uptake ceases. The mixture is then filtered and the bulk of the methanol is removed by evaporation in vacuo. Water and ethyl acetate are added to the residue and the pH is adjusted to 8.5. The layers are separated and the organic layer is washed with water, dried ($Na_2SO_4$) and evaporated in vacuo. This affords pivaloyloxymethyl penicillanate 1,1-dioxide.

EXAMPLE 12

Hydrogenolysis of each of the 6,6-dihalopenicillanic acid ester 1,1-dioxides from Example 10, according to the procedure of Example 11, affords the following compounds:
3-phthalidy penicillanate 1,1-dioxide,
4-crotonolactonyl penicillanate 1,1-dioxide,
gamma-butyrolacton-4-yl penicillanate 1,1-dioxide,
acetoxymethyl penicillanate 1,1-dioxide,
pivaloyloxymethyl penicillanate 1,1-dioxide,
hexanoyloxymethyl penicillanate 1,1-dioxide,
1-(acetoxy)ethyl penicillanate 1,1-dioxide,
1-(isobutyryloxy)ethyl penicillanate 1,1-dioxide,
1-methyl-(acetoxy)ethyl penicillanate 1,1-dioxide,
1-methyl-1-(hexanoyloxy)ethyl penicillanate 1,1-dioxide,
methoxycarbonyloxymethyl penicillanate 1,1-dioxides,
propoxycarbonyloxymethyl penicillanate 1,1-dioxide,
1-(ethoxycarbonyloxy)ethyl penicillanate 1,1-dioxide,
1-(butoxycarbonyl)ethyl penicillanate 1,1-dioxide,
1-methyl-1-(methoxycarbonyloxy)ethyl penicillanate 1,1-dioxide and
1-methyl-1-(isopropoxycarbonyloxy)ethyl penicillanate 1,1-dioxide, respectively.

EXAMPLE 13

Pivaloyloxymethyl 6,6-dibromo-penicillanate 1,1-Dioxide

A stirred solution of 3.92 g of 6,6-dibromo-penicillanic acid 1,1-dioxide in 20 ml of N,N-dimethylformamide was cooled to 0° C. and then 1.29 g of diisopropylethylamine was added. This was followed by 1.51 g of chloromethyl pivalate. This reaction mixture was stirred at 0° C. for 3 hours, and then at room temperature for 16 hours. The reaction mixture was then diluted with 25 ml of ethyl acetate and 25 ml of water. The layers were separated and the aqueous layer was extracted with ethyl acetate. The combined ethyl acetate layers were washed with cold 5% sodium bicarbonate solution, water and brine. The ethyl acetate solution was then treated with Darco (an activated charcoal), dried ($MgSO_4$) and evaporated in vacuo to a brown oil weighing 2.1 g. This oil was chromatographed on 200 g of silica gel, using dichloromethane as eluant. The fractions containing the desired product were combined and rechromatographed on silica gel to give 0.025 g of the title compound. The NMR spectrum ($CDCl_3$) showed absorptions at 6.10 (q, 2H), 5.00 (s, 1H), 4.55 (s, 1H), 1.60 (s, 3H), 1.50 (s, 3H), and 1.15 (s, 9H) ppm.

EXAMPLE 14

Pivaloyloxymethyl Penicillanate 1,1-Dioxide

To a stirred solution of 60 mg of pivaloyloxymethyl 6,6-dibromopenicillanate 1,1-dioxide in 5 ml of benzene was added 52 μl of tri-n-butyltin hydride followed by a catalytic amount of azobisisobutytronitrile. The reaction mixture was cooled to ca 5° C. and then it was irradiated with ultraviolet light for 1 hour. The reaction mixture was poured into 20 ml of cold 5% sodium bicarbonate and stirred for 30 minutes. Ethyl acetate was added and the pH of the aqueous phase was adjusted to 7.0. The layers were separated, and the aqueous phase was further extracted with ethyl acetate. The combined ethyl acetate solutions were washed with brine, dried ($MgSO_4$) and evaporated in vacuo. The residue was dried under high vacuum for 30 minutes. This afforded 70 mg of a yellow oil which was shown by NMR spectroscopy to contain the title compound, together with some impurities containing n-butyl groups.

EXAMPLE 15

6,6-Dibromopenicillanic Acid 1,1-Dioxide

To a solution of 359 mg of 6,6-dibromopenicillanic acid in 30 ml of dichloromethane is added 380 mg of 3-chloroperbenzoic acid at 0°-5° C. The reaction mixture is stirred at 0°-5° C. for 30 minutes and then at 25° C. for 24 hours. The filtered reaction mixture is evaporated in vacuo to give the title compound.

PREPARATION A

6,6-Dibromopenicillanic Acid

To 500 ml of dichloromethane cooled to 5° C. was added 119.9 g of bromine, 200 ml of 2.5N sulfuric acid and 34.5 g of sodium nitrite. To this stirred mixture was then added 54.0 g of 6-aminopenicillanic acid, portionwise over 30 minutes, with the temperature maintained from 4° to 10° C. Stirring was continued for 30 minutes at 5° C., and then 410 ml of a 1.0M solution of sodium bisulfite was added dropwise at 5° to 10° C. during 20 minutes. The layers were separated and the aqueous layer was extracted twice with 150 ml of dichloromethane. The original dichloromethane layer was combined with the two extracts to give a solution of 6,6-dibromopenicillanic acid. This solution was used directly in Example 1.

PREPARATION B

6-Chloro-6-iodopenicillanic Acid

To 100 ml of dichloromethane cooled to 3° C. was added 4.87 g of iodine chloride, 10 ml of 2.5N sulfuric acid and 2.76 g of sodium nitrite. To this stirred mixture was then added 4.32 g of 6-aminopenicillanic acid portionwise during a 15 minute period. Stirring was continued for 20 minutes at 0°-5° C., and then 100 ml of 10% sodium bisulfite solution was added dropwise at ca 4° C. Stirring was continued for 5 minutes and then the layers were separated. The aqueous layer was extracted with dichloromethane (2×50 ml) and the combined dichloromethane solutions were washed with brine, dried (MgSO$_4$) and evaporated in vacuo to give the title compound as a tan solid, mp 148°-152° C. The NMR spectrum of the product (CDCl$_3$) showed absorptions at 5.40 (s,1H), 4.56 (s,1H), 1.67 (s,3H) and 1.50 (s,3H)ppm. The IR spectrum (KBr disc) showed absorptions at 1780 and 1715 cm$^1$.

PREPARATION C

6-Bromo-6-iodopenicillanic Acid

To 100 ml of dichloromethane, cooled to 5° C., was added 10 ml of 2.5N sulfuric acid, 6.21 g of iodine bromide and 2.76 g of sodium nitrite. To this mixture was added, with vigorous stirring, at 0°-5° C., over 15 minutes, 4.32 g of 6-aminopenicillanic acid. Stirring was continued for a further 20 minutes at 0°-5° C., and then 100 ml of 10% sodium bisulfite was added dropwise between 0° and 10° C. At this point, the layers were separated and the aqueous layer was extracted with dichloromethane (3×50 ml). The combined dichloromethane layers were washed with brine, dried (MgSO$_4$) and evaporated in vacuo. The residue was dried under high vacuum for 30 minutes to give 6.0 g (72% yield) of the title compound mp 144°-147° C. The NMR spectrum (CDCl$_3$) showed absorptions at 5.50 (s,1H), 4.53 (s,1H), 1.70 (s,3H) and 1.53 (s,3H)ppm. The IR spectrum (KBr disc) showed absorptions at 1785 and 1710 cm$^1$. The mass spectrum showed a prominent ion at m/e=406.

PREPARATION D

6-Chloro-6-bromopenicillanic Acid

6-Chloro-6-bromopenicillanic acid is prepared from 6-aminopenicillanic acid via diazotzation followed by reaction with bromine chloride, according to the procedure of Preparation C.

PREPARATION E

Pivaloyloxymethyl 6,6-dibromopenicillanate

To a stirred solution of 3.59 g of 6,6-dibromopenicillanic acid in 20 ml of N,N-dimethylformamide is added 1.30 g of diisopropylethylamine followed by 1.50 g of chloromethyl pivalate at ca 0° C. The reaction mixture is stirred at ca 0° C. for 30 minutes and then at room temperature for 24 hours. The reaction mixture is then diluted with ethyl acetate and water and the pH of the aqueous phase is adjusted to 7.5. The ethyl acetate layer is separated and washed three times with water and once with saturated sodium chloride solution. The ethyl acetate solution is then dried using anhydrous sodium sulfate, and evaporated in vacuo to give the title compound.

PREPARATION F

Reaction of the appropriate 6,6-dihalopenicillanic acid with 3-phthalidyl chloride, 4-crotonlactonly chloride, gamma-butyrolaction-4-yl chloride or the requisite alkanoyloxymethyl chloride, 1-(alkanyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkonycarbonyloxy)ethyl chloride, according to the procedure of Preparation E, affords the following compounds:
3-phthalidyl 6,6-dibromopenicillanate,
4-crotonolactonyl 6-chloro-6-iodopenicillanate,
γ-butyrolactonyl 6-bromo-6-iodopenicillanate,
acetoxymethyl 6-chloro-6-bromopenicillanate,
pivaloyoxymethyl 6-chloro-6-iodopenicillanate,
hexanoyloxymethyl 6,6-dibromopenicillanate,
1-(acetoxy)ethyl 6,6-dibromopenicillanate,
1-(isobutyryloxy)ethyl 6-bromo-6-iodopenicillante,
1-methyl-1-(acetoxy)ethyl 6,6-dibromopenicillanate,
1-methyl-1-(hexanoyloxy)ethyl 6-chloro-6-bromopenicillante,
methoxycarbonyloxymethyl 6,6-dibromopenicillanate,
propoxycarbonyloxymethyl 6-chloro-6-iodopenicillanate,
1-(ethoxycarbonyloxy)ethyl 6,6-dibromopenicillanate,
1-(butoxycarbonyloxy)ethyl 6-bromo-6-iodopenicillanate,
1-methyl-1-(methoxycarbonyloxy)ethyl 6,6-dibromopenicillanate and
1-methyl-1-(isopropoxycarbonyloxy)ethyl 6,6-dibromopenicillanate.

What is claimed is:
1. A process for the preparation of a compound of the formula

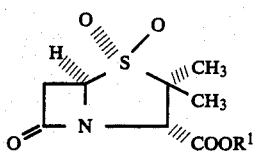

or a pharmaceutically-acceptable base salt thereof, wherein $R^1$ is selected from the group consisting of hydrogen alkanoyloxymethyl having from 3 to 7 carbon atoms, 1-(alkanoyloxy)-ethyl having from 4 to 8 carbon atoms, 1-methyl-1-(alkanoyloxy)ethyl having from 5 to 9 carbon atoms, alkoxycarbonyloxmethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl, which comprises the steps of:

(a) contacting a compound of the formula

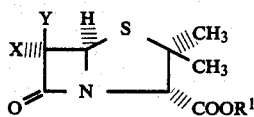

or a base salt thereof with a reagent selected from the group consisting of alkali metal permanganates, alkaline earth metal permanganates and organic peroxycarboxylic acids, to give a compound of the formula

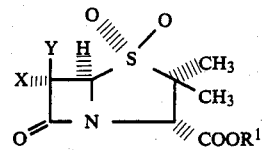

or a base salt thereof, wherein X and Y are each selected from the group consisting of chloro, bromo and iodo; provided that X and Y are not both chloro and X and Y are not both iodo; and (b) contacting the product of step (a) with hydrogen, in an enert solvent, at a pressure in the range from about 1 to about 100 kg/cm², at a temperature in the range from about 0° to about 60° C. at a pH in the range from about 4 to about 9, and in the presence of from about 0.01 to about 2.5 weight-percent of a hydrogenolysis catalyst.

2. The process according to claim 1, wherein X and Y are each bromo.

3. The process according to claim 2, wherein $R^1$ is hydrogen.

4. The process according to claim 3, wherein step (a) is carried out using a reagent selected from the group consisting of alkali metal permanganates and alkaline earth metal permanganates, in a reaction-inert solvent, at a temperature in the range from about −30° to about 50° C.

5. The process according to claim 4, wherein step (a) is carried out using potassium permanganate.

6. The process according to claim 3, wherein step (a) is carried out using an organic peroxycarboxylic acid, in a reaction-inert solvent, at a temperature in the range from about −30° to about 50° C.

7. The process according to claim 6, wherein said peroxycarboxylic acid is 3-chloroperbenzoic acid.

* * * * *